United States Patent
Kellis et al.

(10) Patent No.: US 10,556,030 B2
(45) Date of Patent: Feb. 11, 2020

(54) DISINFECTANT SPRAY CLEANER DISPENSER PACKAGE

(71) Applicant: BISSELL Homecare, Inc., Grand Rapids, MI (US)

(72) Inventors: Jay M. Kellis, Grand Rapids, MI (US); Kevin L. Haley, Byron Center, MI (US)

(73) Assignee: BISSELL Homecare, Inc., Grand Rapids, MI (US)

( * ) Notice: Subject to any disclaimer, the term of this patent is extended or adjusted under 35 U.S.C. 154(b) by 342 days.

(21) Appl. No.: 15/353,231

(22) Filed: Nov. 16, 2016

(65) Prior Publication Data

US 2017/0143860 A1    May 25, 2017

Related U.S. Application Data

(60) Provisional application No. 62/257,503, filed on Nov. 19, 2015.

(51) Int. Cl.

| | |
|---|---|
| *A61L 2/00* | (2006.01) |
| *A61L 9/00* | (2006.01) |
| *B65D 1/40* | (2006.01) |
| *B65D 83/00* | (2006.01) |
| *B65D 35/28* | (2006.01) |
| *A61L 2/22* | (2006.01) |
| *A01N 59/00* | (2006.01) |
| *A01N 25/34* | (2006.01) |

(52) U.S. Cl.
CPC ............... *A61L 2/22* (2013.01); *A01N 25/34* (2013.01); *A01N 59/00* (2013.01); *A61L 2202/15* (2013.01)

(58) Field of Classification Search
CPC ...... A61L 2/186; A61L 2/0082; A61L 2/0088; A01N 27/00; A61J 1/00
USPC .................. 422/292, 300, 305; 222/95, 105; 220/62.21, 402.1; 239/302; 221/64–65
See application file for complete search history.

(56) References Cited

U.S. PATENT DOCUMENTS

| | | | | |
|---|---|---|---|---|
| 5,769,282 A | * | 6/1998 | Lane | .................... B65D 83/625 222/386.5 |
| 7,623,523 B2 | * | 11/2009 | Kondou | ............ H04L 29/06027 370/395.21 |
| 7,632,523 B2 | | 12/2009 | Ramirez et al. | |
| 8,999,400 B2 | | 4/2015 | Ramirez et al. | |
| 2007/0119874 A1 | * | 5/2007 | Geier | .................... B65D 83/42 222/386.5 |
| 2010/0264165 A1 | | 10/2010 | Hansen et al. | |

* cited by examiner

*Primary Examiner* — Monzer R Chorbaji
(74) *Attorney, Agent, or Firm* — McGarry Bair PC

(57) ABSTRACT

A disinfectant spray cleaner dispenser package includes a container, a bag on valve assembly provided with the container, and an enhanced activity aqueous hydrogen peroxide disinfectant solution is stored within a pouch of the bag on valve assembly. The enhanced activity aqueous hydrogen peroxide disinfectant solution has a pH of from about 0.5 to about 6 and includes hydrogen peroxide in a concentration of from about 0.05 to about 8 w/w % of the total solution and at least one anionic surfactant.

10 Claims, 6 Drawing Sheets

DISINFECTANT SPRAY CLEANER DISPENSER PACKAGE

CROSS-REFERENCE TO RELATED APPLICATION(S)

This application claims the benefit of U.S. Provisional Patent Application No. 62/257,503, filed Nov. 19, 2015, which is incorporated herein by reference in its entirety.

BACKGROUND

Disinfectants are often used in cleaning solutions to eliminate or reduce microorganisms on surfaces such as floors, countertops, toys, bathtubs, etc. There are several different types of disinfecting compounds such as alcohols, aldehydes, oxidizing agents, quaternary ammonium compounds and biguanide polymers, for example. The different types of disinfecting compounds have varying degrees of effectiveness against a variety of microorganisms. Hydrogen peroxide is an example of one type of disinfecting compound that can be used to disinfect household surfaces.

Sanitizing compositions containing hydrogen peroxide are corrosive and can degrade various components of a dispenser package, which can cause fluid leakage and lead to premature failure. The presence of certain ingredients or combinations of ingredients within a solution can increase the likelihood of incompatibility with the dispenser package and can render the dispenser package more vulnerable to damage or failure.

BRIEF SUMMARY

In one aspect, the invention relates to a disinfectant spray cleaner dispenser package, including a dispensing container and a bag on valve assembly. An enhanced activity aqueous hydrogen peroxide disinfectant solution is stored within a pouch of the bag on valve assembly. The enhanced activity aqueous hydrogen peroxide disinfectant solution has a pH of from about 0.5 to about 6 and includes hydrogen peroxide in a concentration of from about 0.05 to about 8 w/w % of the total solution and at least one anionic surfactant.

DESCRIPTION OF EMBODIMENTS OF THE INVENTION

Figure 1:
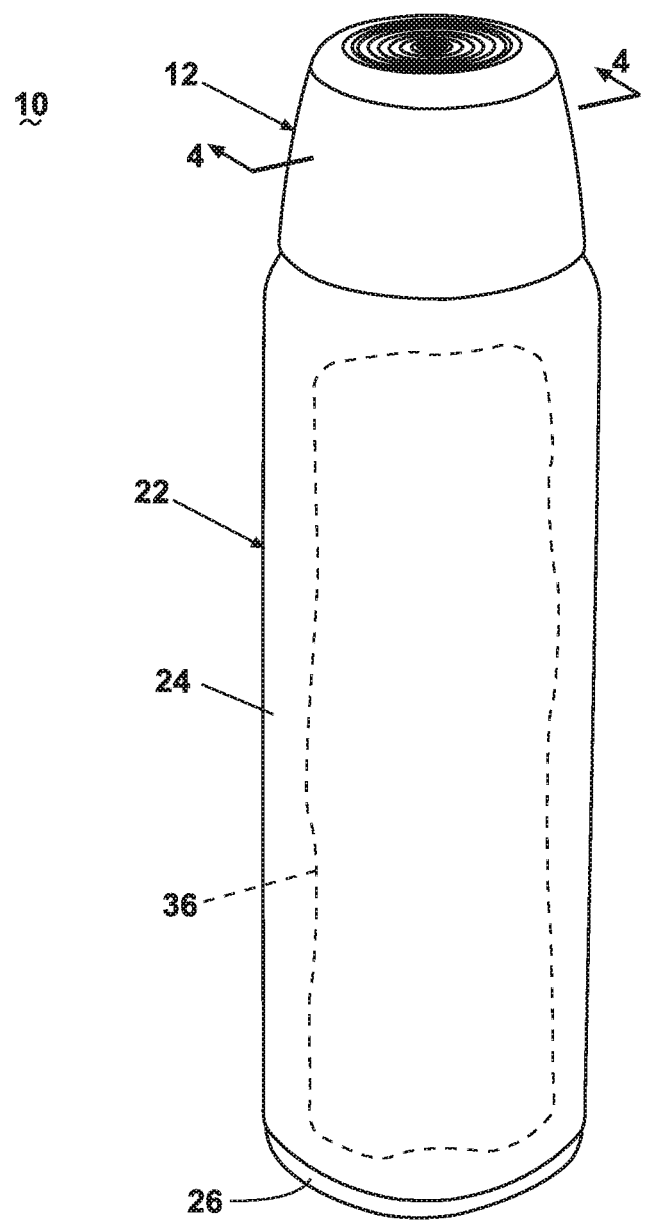
FIG. 1 is a perspective view of a pressurized dispenser assembly according to one embodiment of the invention.

The invention generally relates to a manual spray cleaner dispenser package configured to be chemically compatible with an enhanced activity aqueous hydrogen peroxide disinfectant solution. The spray cleaner dispenser package can be used to apply the solution onto a surface to be treated to eliminate or reduce microorganisms thereon.

Enhanced Activity Aqueous Hydrogen Peroxide Disinfectant Solution

The enhanced activity aqueous hydrogen peroxide disinfectant solution comprises at least hydrogen peroxide and has a pH of from about 0.5 to about 6. Hydrogen peroxide can be present in a concentration of from about 0.05 to about 8 w/w % (mass fraction or % mass/mass) of the total solution. The enhanced activity aqueous hydrogen peroxide disinfectant solution includes a synergistic blend of ingredients with low levels of hydrogen peroxide that dramatically increases its germicidal properties and cleaning ability. A concentration of from about 0.05 to about 8 w/w % for hydrogen peroxide in the disinfectant solution is preferred, because below this range, there is little efficacy, and above this range, is not practical for consumer products and is considered a hazardous material by the DOT.

In a first embodiment, the enhanced activity aqueous hydrogen peroxide disinfectant solution has a pH of from about 0.5 to about 6 and consists essentially of: (i) hydrogen peroxide in a concentration of from about 0.05 to about 8 w/w % of the total solution; and (ii) at least one anionic surfactant selected from the group consisting of C8 to C16 alkyl aryl sulfonic acids and alkali metal, ammonium, ethanolamine, calcium and magnesium salts thereof, sulfonated C12 to C22 carboxylic acids and alkali metal, ammonium, calcium and magnesium salts thereof, C6 to C22 alkyl diphenyl oxide sulfonic acids and alkali metal, ammonium, ethanolamine, calcium and magnesium salts thereof, naphthalene sulfonic acids and alkali metal, ammonium, calcium and magnesium salts thereof, C8 to C22 alkyl sulfonic acids and alkali metal, ammonium, calcium and magnesium salts thereof, alkali metal, ammonium, calcium and magnesium C8 to C18 alkyl sulfates, alkyl or alkenyl esters or diesters of sulfosuccinic acid in which the alkyl or alkenyl groups independently contain from six to eighteen carbon atoms and alkali metal, ammonium, calcium and magnesium salts thereof, and mixtures thereof, in a concentration range of from about 0.02 to about 8 w/w % of the total solution.

Optionally, the enhanced activity aqueous hydrogen peroxide disinfectant solution may further contain: (iii) at least one additional ingredient chosen from a monocarboxylic acid, a polycarboxylic acid, and mixtures thereof, in a concentration of from about 0.05 to about 4 w/w % of the total solution; and (iv) at least one further additional ingredient chosen from benzyl alcohol, an alcohol comprising one to six carbon atoms, and mixtures thereof, in a concentration of from about 0.1 to about 10 w/w % of the total solution.

The enhanced activity aqueous hydrogen peroxide disinfectant solution of the first embodiment is more fully described in U.S. Pat. No. 7,632,523 to Ramirez et al. and assigned to Virox Technologies, Inc., which is incorporated herein by reference in its entirety.

In a second embodiment, an enhanced activity aqueous hydrogen peroxide disinfectant solution has a pH of from about 0.5 to about 6 consists essentially of: (i) hydrogen peroxide in a concentration of from about 0.05 to about 8 w/w % of the total solution; and (ii) at least one anionic surfactant in a concentration of from about 0.02 to about 8 w/w % of the total solution. The at least one anionic surfactant for the second embodiment of the enhanced activity aqueous hydrogen peroxide disinfectant solution can be selected from the group of anionic surfactants listed for the first embodiment. The solution of the second embodiment may further comprise polycarboxylic acid in the form of citric acid and nonionic surfactants.

The enhanced activity aqueous hydrogen peroxide disinfectant solution of the second embodiment is more fully described in U.S. Pat. No. 8,999,400 to Ramirez et al. and assigned to Virox Technologies, Inc., which is incorporated herein by reference in its entirety.

Dispenser Package

The spray cleaner dispenser package can comprise a dispensing container having: a body with a closed bottom and an open upper end forming a neck; and a dispensing valve mounted in the neck. A flexible pouch is mounted within the container and has an open upper end that is sealed to the dispensing valve. An enhanced activity aqueous hydrogen peroxide disinfectant solution is stored in the flexible pouch. A pressurized propellant gas is between the container body and the flexible pouch to pressurize the disinfectant solution within the flexible pouch. Examples of suitable propellant gases are nitrogen and compressed air due to their inert nature and low-impact on the environment as opposed to traditional propellants that are composed of volatile organic compounds (VOCs). The total VOC content for this improved pressurized design can be 0 or within the range of roughly 0-2% by weight.

Additional details of one suitable spray cleaner dispenser package are more fully disclosed in U.S. Patent Application Publication No. 2010/0264165, published Oct. 21, 2010, which is incorporated herein by reference in its entirety. Other dispenser packages utilizing a bag on valve dispenser having a flexible pouch storing the enhanced activity aqueous hydrogen peroxide disinfectant solution can also be used.

In one specific embodiment, the enhanced activity aqueous hydrogen peroxide disinfectant solutions described herein are packaged within a bag on valve dispenser having a flexible pouch comprising multiple layers of flexible material that are laminated together. All layers are hermetically sealed to a valve housing to permanently bond the pouch to the valve housing and the outer edges of the layers form a hermetically sealed edge on the pouch.

In one embodiment, the pouch comprises seven layers of material. The layers of the pouch can comprise, in order from the outermost layer to the innermost layer: a 12 µm polyethylene terephthalate layer; a first 3 µm adhesive layer; an 8 µm aluminum layer; a second 3 µm adhesive layer; a 15 µm oriented polyamide layer; a third 3 µm adhesive layer; and a 75 µm polypropylene layer. It is within the scope of the invention for the pouch to be comprised of different or additional layers. It is also within the scope of the invention for the pouch to have any number of layers made from any suitable material that is essentially inert with respect to the enhanced activity aqueous hydrogen peroxide disinfectant solution as described above. By "essentially inert," the pouch will not be readily degraded by the disinfectant solution after six months at ambient temperature and two months at elevated temperature.

One suitable valve and pouch system can be purchased from SeaquistPerfect Dispensing, a division of AptarGroup, Inc., Cary, Ill.

Figure 2:
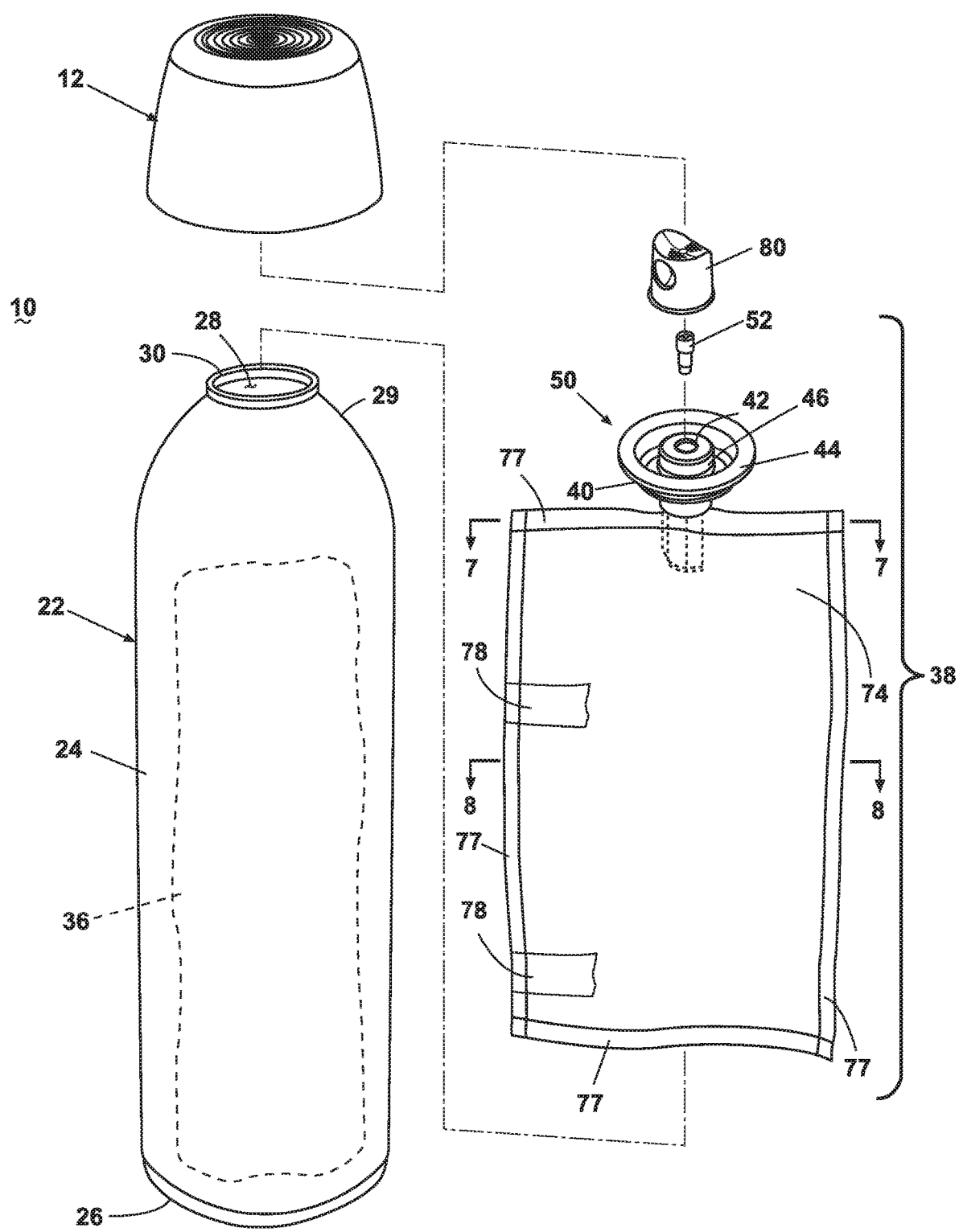
FIG. 2 is an exploded view of the pressurized dispenser assembly shown in FIG. 1.

Referring to FIGS. 1 and 2, one example of a manual spray cleaner dispenser package in the form of a pressurized dispenser 10 is illustrated. The pressurized dispenser comprises a container 22, a bag-on-valve or pouch-on-valve assembly 38 for storing a disinfecting composition and regulating its dispensing, an actuator 80 operably coupled to the pouch-on-valve assembly 38 for selectively dispensing the disinfecting composition onto the surface to be cleaned, and a removable cap 12 that is selectively placed on the container 22 to cover the actuator 80. The pouch-on-valve assembly 38 comprises a pouch 74 received within the container 22 for storing a supply of disinfecting composition and a valve assembly 50 that is hermetically sealed to the pouch 74 and on which the actuator 80 is mounted. The valve assembly further comprises a valve mounting cup 40 that mounts the pouch-on-valve assembly 38 to the container 22.

Figure 3:
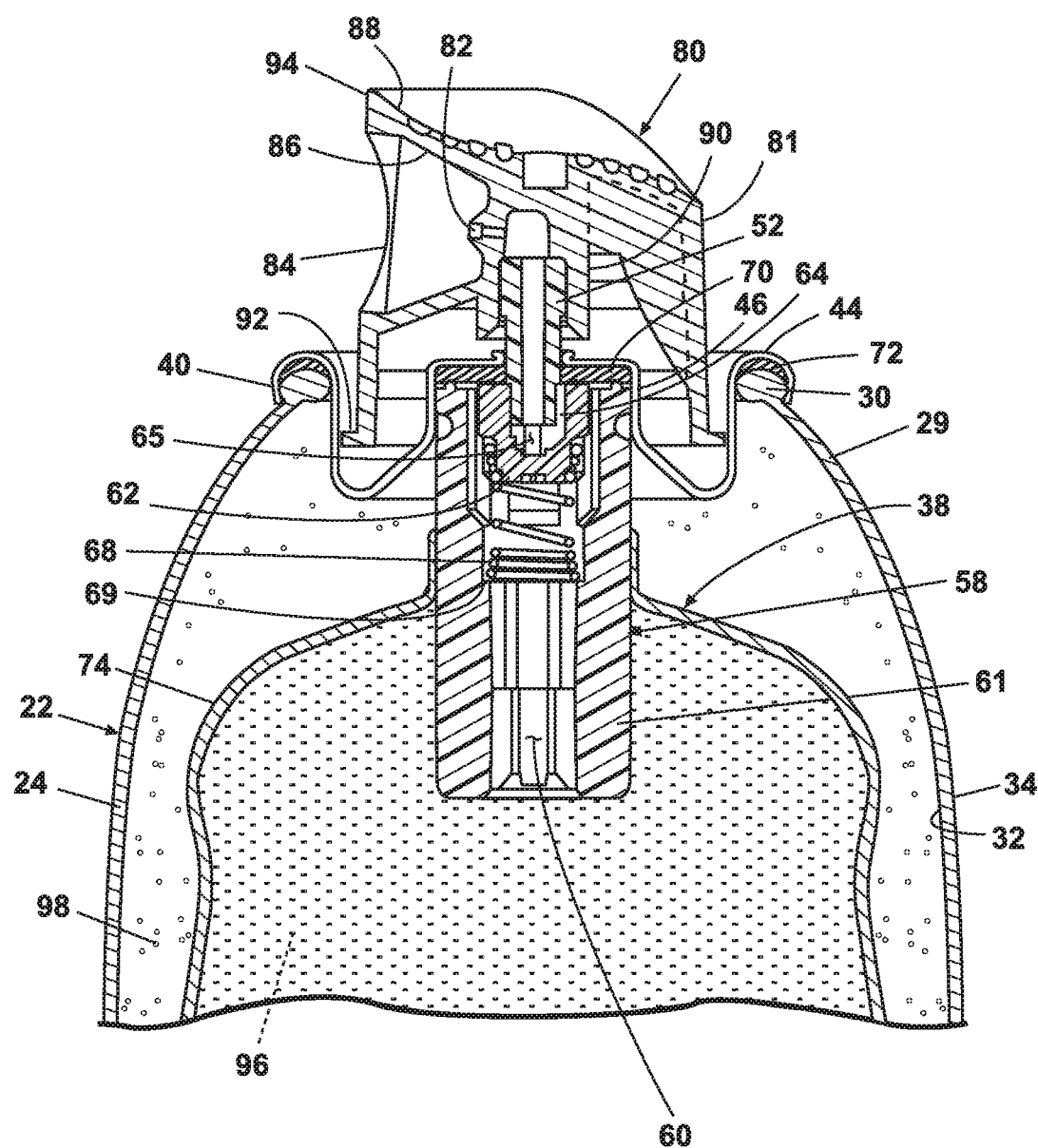
FIG. 3 is a partial section view taken along line 4-4 of FIG. 1.

Referring to FIG. 3, a disinfecting composition 96 is contained within the pouch 74, and a quantity of compressed propellant gas 98 is contained within the can assembly 22 surrounding the pouch 74 to provide propellant force necessary to dispense the disinfecting composition 96 from the dispenser 10. The disinfecting composition 96 can comprise an enhanced activity aqueous hydrogen peroxide disinfectant solution as described above.

The disinfecting composition 96 is delivered to the surface to be cleaned via the actuator 80, which is in fluid communication with the push valve assembly 50 (FIG. 2) that is sealed to the flexible pouch 74 containing the disinfecting composition. The flexible pouch 74 containing the disinfecting composition 96 resides within the metal can assembly 22. Positive pressure inside the can assembly 22 is generated by the propellant gas 98 that is injected during the can filling process. The propellant gas 98 is filled to a level sufficient for generating the required force to deliver the disinfecting composition 96 to the surface to be cleaned with a spray character, i.e. the force of the spray, the diameter of the spray, the type of particle sprayed, etc. that is desirable for the intended application.

Referring to FIGS. 2, and 3, the container 22 comprises a body 24 that is generally cylindrical in shape with a closed bottom 26 and an open upper end 28 formed in an inwardly curving neck 29 of the body 24. The neck 29 further comprises a bead 30 defining the periphery of the open upper end 28. The container 22 includes an inner surface 32 and an outer surface 34 on which a polymer coating can be applied. The container 22 may also include an optional lithograph label 36 applied to the outer can surface 32 for decorative purposes such as product use and marketing communications. The container 22 can be manufactured of polymer-coated tin free steel stock T3CA temper with a nominal thickness of about 0.23 mm (0.009 inches). The polymer coating on the inner and outer surfaces 32 and 34 can comprise polyethylene terephthalate (PET) film which offers an improved aesthetic appearance and may also provide corrosion inhibiting properties.

Figure 4:
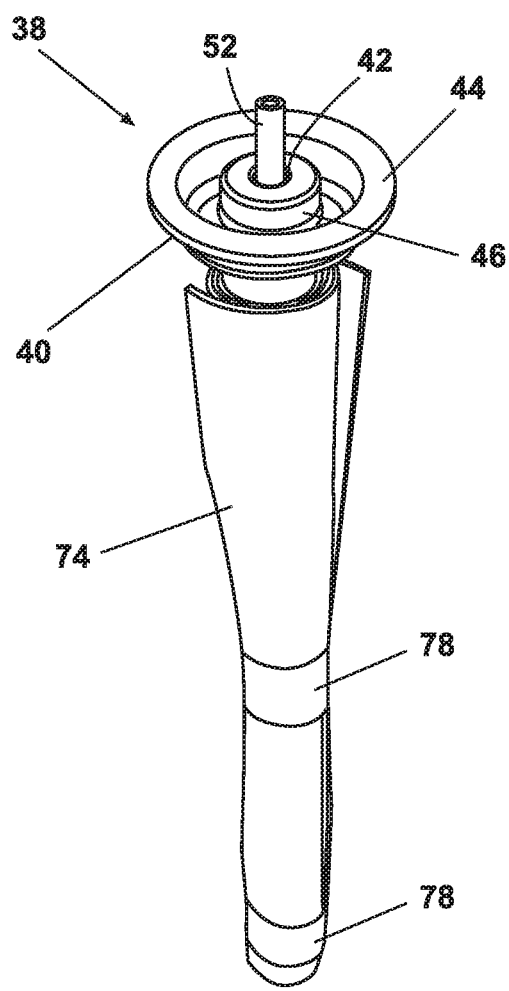
FIG. 4 is a perspective view of a pouch-on-valve assembly of the dispenser assembly shown in FIG. 2.

Referring to FIGS. 3 and 4, the valve mounting cup 40 is mounted within the open end 28 of the container 22 to mount the pouch-on-valve assembly 38 within the container 22 and to close the open end 28. The valve mounting cup 40 comprises a central cylindrical protrusion 46 having a dispensing opening 42 therein and an annular lip 44 formed on the periphery of the valve mounting cup 40. The annular lip 44 is sized to receive and seal the open end 28 of the container 22. The annular lip 44 further includes a gasket 72 to insure a leak proof seal to the bead 30 formed on the container 22. The valve mounting cup 40 can be manufactured of a tin steel material. The gasket 72 can be comprised of a butyl rubber material.

Figure 5:
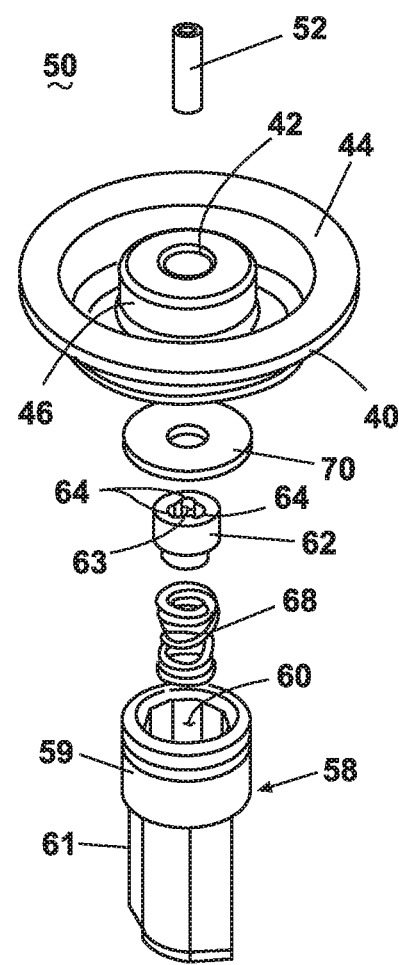
FIG. 5 is an exploded view of a valve assembly of the dispenser assembly shown in FIG. 2.
Figure 6:
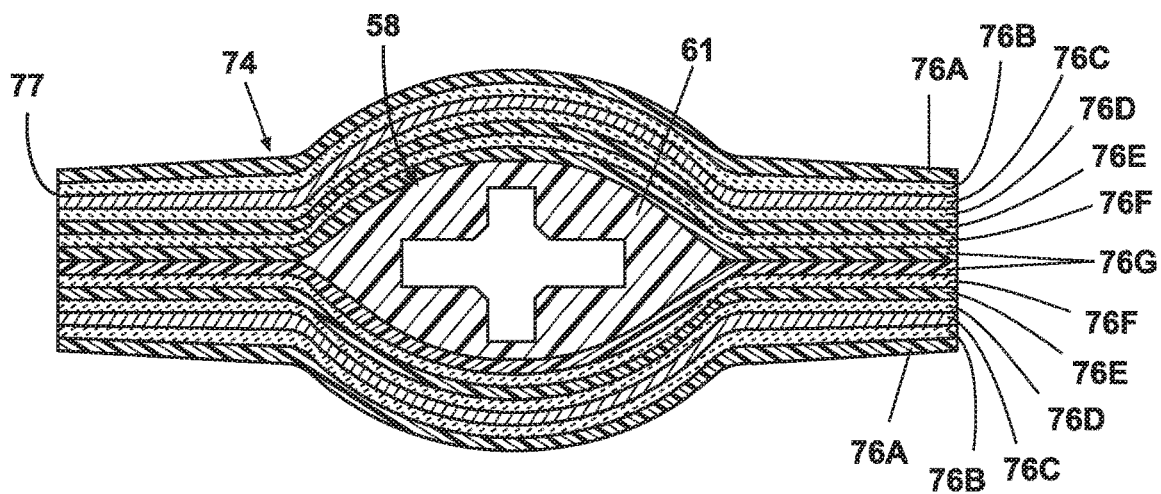
FIG. 6 is a partial section view taken along line 7-7 of FIG. 2.

Referring to FIGS. 3 and 5, the valve assembly 50 further comprises a valve housing 58 that receives a hollow valve stem 52 having a solid plunger 62 mounted to a lower end thereof. The valve housing 58, which is preferably injection molded polypropylene material, comprises a hollow cylindrical upper portion 59 and a reduced diameter hollow lower valve body portion 61, with a fluid flow channel 60 formed therethrough that is in fluid communication with the disinfecting composition 96 within the pouch 74. The exterior shape of the lower valve body portion 61 forms an eye-shaped cross-section, as shown in FIG. 6. This shape facilitates sealing ability the valve housing 58 and the flexible pouch 74.

The plunger 62 is received within the protrusion 46 of the valve mounting cup 40, with the valve stem 52 extending through the dispensing opening 42. The plunger 62 comprises a central opening 63 having a closed bottom end and an open top end. Three evenly spaced vertical channels are provided on the central opening 63 and form fluid flow orifices 64 when the plunger 62 is assembled with the valve stem 52 that are in fluid communication with the hollow valve stem 52 via a space 65 formed between the bottom end of the valve stem 52 and the closed bottom of the central opening 63.

The plunger 62 is biased by a compression spring 68 to the closed position of the valve assembly shown in FIG. 3. The compression spring 68, which can be comprised of INOX AISI 302 stainless steel material, is positioned between a support rib 69 formed within the valve housing 58 and the solid plunger 62. A gasket 70 is located between the valve housing 58 and the valve mounting cup 40 and forms a valve seat for the plunger 62. The gasket 70 can be a butyl rubber. Alternative suitable gasket materials can include: buna-nitrile (buna-n), rubber, ethylene propylene diene monomer rubber (EPDM), or fluoropolymer elastomers such as Viton®.

The valve stem 52 can be manufactured using an injection molded polyethylene material chosen for its chemical resistivity. The plunger 62 can be manufactured using an injection molded acetal material.

Figure 7:
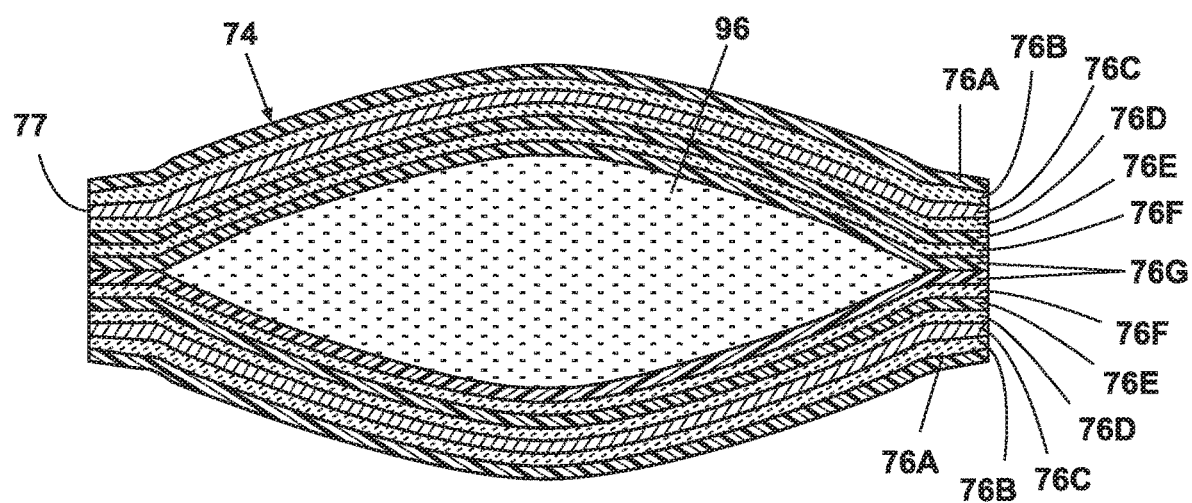
FIG. 7 is a section view taken along line 8-8 of FIG. 2.

As shown in FIGS. 6 and 7, the pouch 74 comprises multiple layers 76 of flexible material that are laminated together. As shown herein, the pouch comprises seven layers 76A-76G of material. The layers 76 of the pouch 74 can comprise, in order from the outermost layer to the innermost layer: a 12 μm polyethylene terephthalate layer 76A; a first 3 μm adhesive layer 76B; an 8 μm aluminum layer 76C; a second 3 μm adhesive layer 76D; a 15 μm oriented polyamide layer 76E; a third 3 μm adhesive layer 76F; and a 75 μm polypropylene layer 76G.

All layers 76 are hermetically sealed to the lower portion 61 of the valve housing 58, as shown in FIGS. 3 and 6. The external dimensions of the pouch 74 are nominally 180 mm tall by 115 mm wide (7.09 inches by 4.53 inches) and, when filled, 70 mm (2.76 inches) deep. The fill volume of the pouch 74 is nominally 400 ml (13.5 fluid oz.). The outer edges of the layers 76 are sealed by a heat seal bonding process that uses heat and pressure to permanently bond the edges of the layers 76 to form a hermetically sealed edge 77 on the pouch 74. The pouch 74 is subsequently sealed to the valve housing 58 by a heat seal bonding process that uses heat and pressure to permanently bond the pouch 74 to the valve housing 58. It is within the scope of the invention for the pouch 74 to be comprised of different or additional layers. It is also within the scope of the invention for the pouch 74 to have any number of layers made from any suitable material.

Referring to FIG. 3, the actuator 80 comprises a sidewall 81 with a circular base 92 that has a larger diameter than a top surface 94. The top surface 94 further includes a curved depression 88 suitable for mating to a user's fingertip. Extending vertically downward from the top surface 94 is a hollow cylinder 90 having a spray tip orifice 82 that is surrounded by a conically-shaped cut-out 86 formed in the sidewall 81. The hollow cylinder 90 fluidly couples the actuator 80 to the valve stem 52, thereby creating a fluid connection between the spray tip orifice 82 and the flexible pouch 74 containing the disinfecting composition 96. The spray tip orifice 82 is surrounded by a conically-shaped cut-out 86 formed in the sidewall 81, which has a terminal aperture 84 defined in the side wall 81.

In one embodiment, the shape of the spray tip orifice 82 comprises a circular through-hole with diameter of 0.51 mm (0.020 inches), which has been found to be effective for application of the disinfecting composition 96 in a relatively small diameter for treating small stains and spills on the surface to be cleaned. The spray tip orifice 82 can comprise any number of alternate shapes depending on the desired spray pattern (for example straight line stream, fan shaped, conical patterns, and the like). A combination of the size of the spray tip orifice 82, the size of the terminal aperture 84, and the pressure of the gas propellant 98 can be optimized to achieve the desired spray flow rate and spray pattern of the disinfecting composition 96. In one non-limiting example, the spray rate can be 5.5 grams/second (0.19 ounce/second) of disinfecting composition, with a range of 5.0 to 6.0 grams/second (0.18 to 0.21 ounce/second) and the preferred spray pattern as measured at roughly 61 cm (24 inches) from the target surface to produce a "forceful stream".

Since the chemical composition of the invention is an enhanced activity aqueous hydrogen peroxide disinfectant solution, it should be understood that all surfaces of the dispenser 10 that come into contact with the disinfecting composition can be manufactured from materials selected for their known resistance to the components of the disinfectant solution. For example, the actuator 80 can comprise an injection molded acetal resin. However, other materials can be used to manufacture the components of the dispenser 10, depending on the disinfecting composition 96 used with the dispenser 10.

Figure 8:
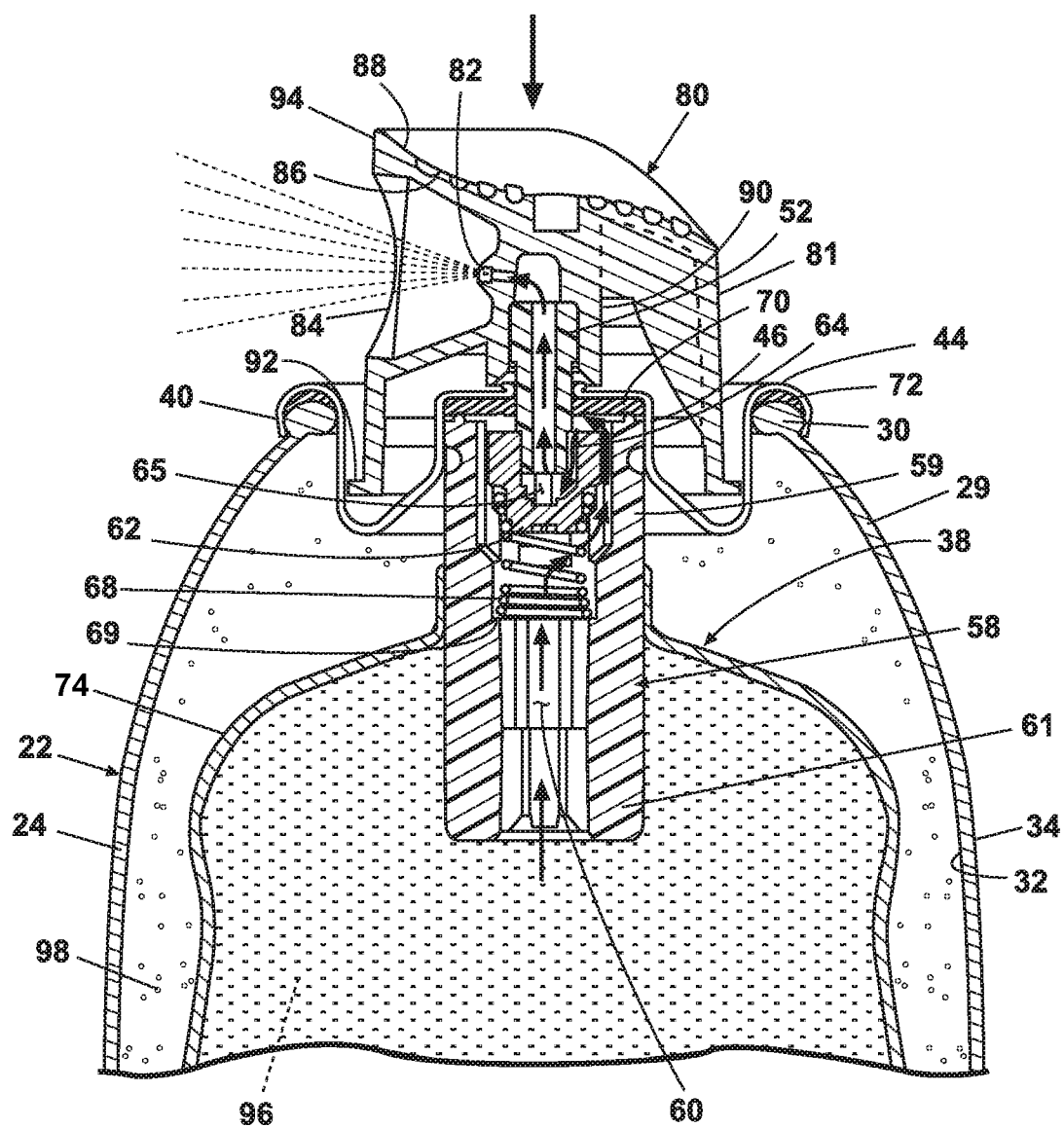
FIG. 8 is a view like FIG. 3 of a partial section view of the pressurized dispenser of FIG. 1 illustrating the operation of the dispenser.

Referring to FIG. 8, in use, the disinfecting composition 96 can be dispensed onto a target surface to be cleaned by depressing the actuator 80 and subsequently creating a fluid flow path between the pouch 74 and the spray tip orifice 82. Depressing the actuator 80 forces the plunger 62 downward, compressing the spring 68, and breaking the seal between the plunger 62 and the gasket 70 to create a space between the gasket 70 and the plunger 62, thereby allowing fluid to flow from the fluid flow channel 60 to the valve stem 52 through the fluid flow orifices 64. The compressed propellant gas 98 induces a positive pressure inside the container 22 and compresses the pouch 74, thereby forcing the disinfecting composition 96 out of the pressurized container 22 to be sprayed out of the spray tip orifice 82. When downward pressure on the actuator 80 is released, the spring 68 forces the plunger 62 and valve stem 52 upward. The plunger 62 seals against the internal gasket 70 and ceases the flow of the disinfecting composition 96. A user can hold the dispenser 10 in various orientations during use, such as upright, inverted, sideways, etc., and still achieve the same dispensing action.

Results

Surprising and unexpected results occur when the enhanced activity aqueous hydrogen peroxide disinfectant solutions described herein are packaged within a bag on valve dispenser having a flexible pouch comprising materials in the configuration disclosed herein. Disinfectant solutions containing hydrogen peroxide can be corrosive and can present a hostile environment for packaging, including the flexible pouch of a bag on valve dispenser. With respect to bag on valve dispensers, the conventional thinking was that the integrity of the flexible pouch would be compromised by disinfectant solutions, causing leaks and inhibiting proper function of the dispenser. As such, this type of disinfecting solution has not been successfully held in a pressurized (aerosol) package.

EXAMPLES

Testing has shown that the flexible pouch can be particularly vulnerable and incompatible with acids contained within the enhanced activity aqueous hydrogen peroxide disinfectant solutions described herein. In certain instances, the presence of specific acids within the composition caused the pouch to fail prematurely by delamination. That is, one or more of the seven layers of pouch material that are bonded together became separated, corroded, and can potentially break and cause leaks in the pouch.

The following examples illustrate some compatibility test results between the pouch and different compositions of the enhanced activity aqueous hydrogen peroxide disinfectant solution. Three different compositions were tested, and each was tested according to a first test referred to as the "Elevated Temperature Compatibility Test" and a second test referred to as the "Ambient Temperature Compatibility Test," both of which are described below. The disinfecting compositions were filled into the pouch 74 of the pressurized dispenser 10 described above. Two compositions were formulated according to U.S. Pat. No. 7,632,523—Composition 1 and Composition 3. One salient difference between these compositions is that Composition 1 lacked certain ingredients that Composition 3 contained, namely a monocarboxylic acid, a polycarboxylic acid, and mixtures thereof, that is present in Composition 3 in a concentration of from about 0.05 to about 4 w/w of the total solution. More specifically, Composition 1 lacked two monocarboxylic acid ingredients: 2-furoic acid and salicylic acid, whereas Composition 3 contained those ingredients. An additional composition, referred to as Composition 2, was formulated according to U.S. Pat. No. 8,999,400. Composition 2 also lacked a monocarboxylic acid, a polycarboxylic acid, and mixtures thereof, in a concentration of from about 0.05 to about 4 w/w % of the total solution and, more specifically, did not contain two monocarboxylic acid ingredients: 2-furoic acid and salicylic acid. It is noted that Composition 1 and 2 both contained some tricarboxylic (polycarboxylic) acid, namely, citric acid. For Composition 1, the citric acid was present in a concentration of 0.8 w/w % of the total solution and for Composition 2, the citric acid was present in a concentration of 0.5 w/w % of the total solution and For the "Elevated Temperature Compatibility Test," the test procedure includes the following storage and analysis steps: (i) Store (72) bag on valve dispenser packages containing an enhanced activity aqueous hydrogen peroxide disinfectant solution in test oven at 120 degrees Fahrenheit (approximately 49 degrees Celsius); and (ii) Remove and analyze (18) dispensers at intervals of 1, 2, 3, and 4 months as follows. Spray until empty and then cut (18) bag on valve dispenser cans. Evaluate material appearance and odor compared to standard sample. Perform visual assessment of all bag on valve components using a stereo microscope. Evaluate and document bag interior condition, noting any deterioration found. Evaluate other components (spring, spring seat, and stem) for any degradation. Note any issues or anomalies observed during spraying.

For the "Ambient Temperature Compatibility Test," the test procedure includes the following storage and analysis steps: (i) Store (72) bag on valve dispenser packages containing an enhanced activity aqueous hydrogen peroxide disinfectant solution at ambient temperature (approximately 72±2 degrees Fahrenheit); and (ii) Analyze (18) dispensers at intervals of 3, 6, 9, and 12 months as follows. Spray until empty and then cut (18) room temperature cans. Evaluate material appearance and odor compared to standard sample. Perform visual assessment of all bag on valve components using a stereo microscope. Evaluate and document bag interior condition, noting any deterioration found. Evaluate other components (spring, spring seat, and stem) for any degradation. Note any issues or anomalies observed during spraying.

Example 1

Composition 1—Elevated Temperature Compatibility Test

| Test Result | PASSED |
|---|---|
| 1 Month | Very minor delamination |
| 2 Months | Very minor delamination |
| 3 Months | Significant delamination, but no corrosion of aluminum layer 76C |
| 4 Months | Near complete delamination of the two innermost layers - oriented polyamide layer 76E and the polypropylene layer 76G. Some delamination of the outer two layers - polyethylene terephthalate layer 76A and aluminum layer 76C. |

Example 2

Composition 1—Ambient Temperature Compatibility Test

| Test Result | PASSED |
|---|---|
| 3 Months | No visual changes observed. Pouches are pristine. |
| 6 Months | Very small point of delamination on pouch. |
| 9 Months | Moderate delamination in seam areas. No corrosion of aluminum layer 76C. |
| 12 Months | Moderate delamination in seam areas. Minor corrosion of aluminum layer 76C on some pouches. |

Example 3

Composition 2—Elevated Temperature Compatibility Test

| Test Result | PASSED |
|---|---|
| 1 Month | Minor discoloration in seam areas. No corrosion of aluminum layer 76C. |
| 2 Months | Minor discoloration in seam areas. No delamination. |
| 3 Months | Minor discoloration in seam areas of aluminum layer 76C. No delamination |
| 4 Months | Minor delamination in seam areas. |

Example 4

Composition 2—Ambient Temperature Compatibility Test

| Test Result | PASSED |
|---|---|
| 3 Months | No visual changes observed. Pouches are pristine condition. |
| 6 Months | No visual changes observed. Pouches are pristine condition. |
| 9 Months | No visual changes observed. Pouches are pristine condition. |
| 12 Months | Very minor delamination in seam areas. |

Example 5

Composition 3—Elevated Temperature Compatibility Test

| Test Result | FAILED |
|---|---|
| 1 Month | Delamination of pouch layers observed. Some discoloration of aluminum layer 76C observed. Some separation of seams around perimeter. |
| 2 Months | Near complete delamination of innermost two layers, oriented polyamide layer 76E and polypropylene layer 76G. Discoloration between oriented polyamide layer 76E and aluminum layer 76C. Significant seam separation. |
| 3 Months | Very excessive delamination of aluminum layer 76C. Extensive delamination in seam areas. |
| 4 Months | N/A - test terminated prior to 4 month check interval. |

Example 6

Composition 3—Ambient Temperature Compatibility Test

| Test Result | FAILED |
|---|---|
| 3 Months | Moderate delamination and discoloration of aluminum layer 76C. Some delamination of seams around perimeter. |
| 6 Months | N/A - test terminated after 3 month check interval. |
| 9 Months | N/A - test terminated after 3 month check interval. |
| 12 Months | N/A - test terminated after 3 month check interval. |

The results show that Composition 2 is most compatible with the flexible pouch of the bag on valve dispenser. In both the Elevated. Temperature Compatibility Test and the Ambient Temperature Compatibility Test, only minor or very minor delamination was observed in the seam areas of the pouch. In contrast, Composition 1 experienced moderate to near complete delamination by the end of the tests, while Composition 3 experienced delamination to a sufficient degree to terminate the tests before completion. The near pristine condition of the flexible pouch of the bag on valve dispenser that were test for Composition 2 was surprising, as it was expected that all of the compositions would degrade the flexible pouch.

While the invention has been specifically described in connection with certain specific embodiments thereof, it is to be understood that this is by way of illustration and not of limitation. Reasonable variation and modification are possible with the scope of the foregoing disclosure and drawings without departing from the spirit of the invention which, is defined in the appended claims. Hence, specific dimensions and other physical characteristics relating to the embodiments disclosed herein are not to be considered as limiting, unless the claims expressly state otherwise.

What is claimed is:

1. A disinfectant spray cleaner dispenser package, comprising:
    a dispensing container;
    a bag on valve assembly comprising a dispensing valve mounted to the dispensing container and a flexible pouch within the dispensing container and having an open end that is sealed to the dispensing valve, the flexible pouch including multiple layers of flexible material with each of the multiple layers of flexible material interspersed with an adhesive layer, wherein each of the multiple layers of flexible material interspersed with an adhesive layer comprise multiple laminated layers and the multiple layers of flexible material interspersed with an adhesive layer comprise at least:
    a) a polyethylene terephthalate layer,
    b) an aluminum layer,
    c) a polyamide layer,
    d) a polypropylene layer, and
    e) an adhesive layer between each of the layers a, b, c, and d; and an enhanced activity aqueous hydrogen peroxide disinfectant solution within the flexible pouch, wherein the enhanced activity aqueous hydrogen peroxide disinfectant solution has a pH of from about 0.5 to about 6 and comprises:
    hydrogen peroxide in a concentration of from about 0.05 to about 8 w/w % of the total solution; and
    at least one anionic surfactant.

2. The disinfectant spray cleaner dispenser package of claim 1, wherein the enhanced activity aqueous hydrogen peroxide disinfectant solution does not contain monocarboxylic acid, in a concentration of from about 0.05 to about 4 w/w % of the total solution.

3. The disinfectant spray cleaner dispenser package of claim 1, wherein the enhanced activity aqueous hydrogen peroxide disinfectant solution does not contain 2-furoic acid or salicylic acid.

4. The disinfectant spray cleaner dispenser package of claim 1, wherein the enhanced activity aqueous hydrogen peroxide disinfectant solution comprises citric acid.

5. The disinfectant spray cleaner dispenser package of claim 1, wherein the at least one anionic surfactant is present in a concentration of 0.02 to 8 w/w % of the total solution.

6. The disinfectant spray cleaner dispenser package of claim 5, wherein the at least one anionic surfactant is selected from the group consisting of:
    C8 to C16 alkyl aryl sulfonic acids or alkali metal salts, ammonium salts, ethanolamine salts, calcium salts, or magnesium salts thereof;
    sulfonated C12 to C22 carboxylic acids or alkali metal salts, ammonium salts, calcium salts, or magnesium salts thereof;
    C6 to C22 alkyl diphenyl oxide sulfonic acids or alkali metal salts, ammonium salts, ethanolamine salts, calcium salts, or magnesium salts thereof;
    naphthalene sulfonic acids and alkali metal salts, ammonium salts, calcium salts, or magnesium salts thereof;
    C8 to C22 alkyl sulfonic acids or alkali metal salts, ammonium salts, calcium salts or magnesium salts thereof;
    alkali metal, ammonium, calcium or magnesium C8 to C18 alkyl sulfates; and
    alkyl esters, alkenyl esters, or diesters of sulfosuccinic acid in which the alkyl or alkenyl groups independently contain from six to eighteen carbon atoms or alkali metal salts, ammonium salts, calcium salts, or magnesium salts thereof.

7. The disinfectant spray cleaner dispenser package of claim 1, wherein dispensing container further comprises a pressurized gas between the dispensing container and the flexible pouch to pressurize the disinfectant solution within the flexible pouch.

8. The disinfectant spray cleaner dispenser package of claim 1, wherein the flexible pouch is essentially inert with respect to the disinfectant solution.

9. The disinfectant spray cleaner dispenser package according to claim 1, wherein at least one of the multiple laminated layers is a metallic layer.

10. A disinfectant spray cleaner dispenser package, comprising:
a dispensing container;
a bag on valve assembly comprising a dispensing valve mounted to the dispensing container and a flexible pouch within the dispensing container and having an open end that is sealed to the dispensing valve the dispensing pouch including multiple layers of flexible material laminated together with adhesive to define multiple laminated layers, the multiple layers of flexible material laminated together with adhesive comprise at least: a) a polyethylene terephthalate layer, b) an aluminum layer, c) a polyamide layer, d) a polypropylene layer, and e) an adhesive layer between each of the layers a, b, c and d and wherein outer edges of the layers form a hermetically sealed edge on the pouch; and
an enhanced activity aqueous hydrogen peroxide disinfectant solution within the flexible pouch, wherein the enhanced activity aqueous hydrogen peroxide disinfectant solution has a pH of from about 0.5 to about 6 and comprises:
hydrogen peroxide in a concentration of from about 0.05 to about 8 w/w % of the total solution; and
at least one anionic surfactant.

* * * * *